United States Patent [19]

Goetz et al.

[11] 4,283,534

[45] Aug. 11, 1981

[54] REDUCTIVE ALKYLATION OF NITROGEN HETEROCYCLES

[75] Inventors: Norbert Goetz, Worms; Leopold Hupfer, Friedelsheim, both of Fed. Rep. of Germany

[73] Assignee: BASF Aktiengesellschaft, Fed. Rep. of Germany

[21] Appl. No.: 130,448

[22] Filed: Mar. 14, 1980

[30] Foreign Application Priority Data

Apr. 11, 1979 [DE] Fed. Rep. of Germany ....... 2914646
Sep. 27, 1979 [DE] Fed. Rep. of Germany ....... 2939060

[51] Int. Cl.³ ................ C07D 265/28; C07D 295/02; C07D 295/08
[52] U.S. Cl. ..................................... 544/174; 544/178; 544/398; 544/403; 546/192; 546/236; 260/239 A; 260/239 B; 260/326.5 M; 260/326.87
[58] Field of Search ............. 544/178, 174, 398, 403; 546/236, 192; 260/239 B, 326.5 M, 326.87; 564/398

[56] References Cited

U.S. PATENT DOCUMENTS 2,976,321  3/1961  Dorsky et al. ...................... 424/333

FOREIGN PATENT DOCUMENTS 1179947 10/1964 Fed. Rep. of Germany .
2118283 11/1972 Fed. Rep. of Germany .
2656747  6/1978 Fed. Rep. of Germany .
2752096  6/1978 Fed. Rep. of Germany .
2752135  5/1978 Fed. Rep. of Germany .
2830999  7/1978 Fed. Rep. of Germany .
1396985  6/1975 United Kingdom .

OTHER PUBLICATIONS

Houben-Weyl, *Met. der Org. Chemie*, vol. 4/2 (1955), pp. 328, 329; vol. 11/1 (1957), pp. 602 and 643.
Emerson, "The Preparation of Amines by Reductive Alkylation", *Organic Reactions*, vol. 4 (1962), pp. 174-255.

*Primary Examiner*—Henry R. Jiles
*Assistant Examiner*—R. W. Ramsuer
*Attorney, Agent, or Firm*—Keil & Witherspoon

[57] ABSTRACT

A process for the preparation of aralkylamines of the formula

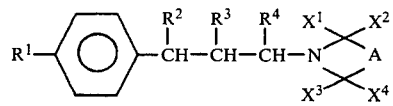

where
$R^1$ is hydrogen, an aliphatic hydrocarbon radical, a cycloaliphatic radical or alkoxy,
$R^2$, $R^3$ and $R^4$ are hydrogen or alkyl,
$X^1$, $X^2$, $X^3$ and $X^4$ are hydrogen or alkyl,
A is

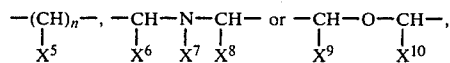

$X^5$, $X^6$, $X^7$, $X^8$, $X^9$ and $X^{10}$ are hydrogen or alkyl and n is 2, 3 or 4, by reacting a secondary amine with a carbonyl compound in the presence of hydrogen and of a hydrogenation catalyst which comprises palladium, mixed with zinc, cadmium, manganese and/or a rare earth metal oxide, on an inert carrier.

1 Claim, No Drawings

REDUCTIVE ALKYLATION OF NITROGEN HETEROCYCLES

The present invention relates to a process for the preparation of aralkylamines by reacting aralkenals or aralkanals with secondary amines.

It is known that tertiary amines may be obtained by reacting secondary amines with carbonyl compounds in the presence of hydrogen and a hydrogenation catalyst (Houben-Weyl "Methoden der organischen Chemie" 4/2, pages 328 et. seq., 11/1, pages 602 et seq. and pages 643 et seq.). German Pat. No. 1,179,947 describes the synthesis of N-alkylated aromatic amines by reductive alkylation of aromatic amines over a palladium/silver catalyst under conditions where the aromatic system is not attacked. According to German Laid-Open Application DOS No. 2,118,283, a palladium/silver catalyst can also be used to prepare tertiary aliphatic or cycloaliphatic amines by reacting aliphatic or cycloaliphatic carbonyl compounds with secondary amines in the presence of hydrogen. The advantage of the particular catalyst is that it can be used to carry out the reductive alkylation of secondary amines with saturated carbonyl compounds in high yield, and substantially without formation of by-products. Suitable carbonyl compounds mentioned particularly are saturated ketones, eg. acetone, methyl ethyl ketone, cyclopentanone and cyclohexanone, and in principle also aldehydes which undergo aldol condensation only with difficulty, if at all, eg. formaldehyde, isobutyraldehyde and 2-ethylhexanal. German Patent Application No. P 2,830,999 describes the preparation of stereoisomeric N-aralkyl-2,6-dimethylmorpholines by reacting stereoisomeric 2,6-dimethylmorpholines with carbonyl compounds in the presence of hydrogen and of a palladium/silver catalyst.

We have found that a tertiary amine of the formula I

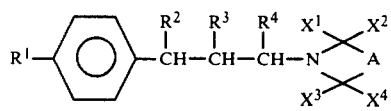

where
$R^1$ is hydrogen, an aliphatic hydrocarbon radical of 1 to 10 carbon atoms, a cycloaliphatic radical of 5 to 7 carbon atoms or alkoxy of 1 to 6 carbon atoms,
$R^2$, $R^3$ and $R^4$ are hydrogen or alkyl of 1 to 4 carbon atoms,
$X^1$, $X^2$, $X^3$ and $X^4$ are hydrogen or alkyl of 1 to 4 carbon atoms,
A is

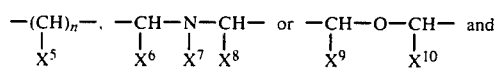

$X^5$, $X^6$, $X^7$, $X^8$, $X^9$ and $X^{10}$ are hydrogen or alkyl of 1 to 4 carbon atoms and
n is 2, 3 or 4,
may be obtained in a simple manner by reacting a secondary amine of the formula II

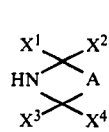

where
$X^1$, $X^2$, $X^3$, $X^4$ and A have the above meanings with a carbonyl compound of the formula III

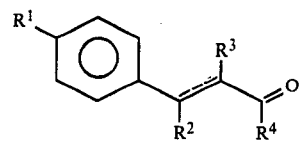

where
$R^1$, $R^2$, $R^3$ and $R^4$ have the above meanings and the bond shown in broken lines is a double bond or a single bond,
if the reaction is carried out in the presence of hydrogen and of a hydrogenation catalyst which comprises palladium, mixed with zinc, cadmium, manganese and/or a rare earth metal oxide, on an inert carrier. The inert carrier may be, for example, alumina, silica or active charcoal. The reaction is carried out at, for example, from 10° to 200° C., advantageously from 20° to 160° C., under atmospheric pressure or pressures of up to 300 bar.

The advantage of the process according to the invention is that particularly sensitive carbonyl compounds, such as α,β-unsaturated aldehydes or ketones, which might undergo adduct formation with amines at the double bonds and would then give a mixture of end products, or aldehydes or ketones, which might undergo aldol condensations, can be used and give single end products. A further advantage of the process according to the invention is that because of the high selectivity of the catalysts employed, the desired end products of the formula I are obtained in a very pure form. Thus, the by-products to be expected from this type of reaction, for example the alcohols of the formula

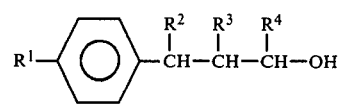

which would result from hydrogenation of the carbonyl compounds, or unsaturated amines of the formula

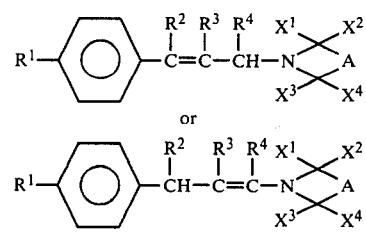

are hardly formed.

If a less selective catalyst, for example a conventional palladium/silver catalyst (German Pat. No. 1,179,947, German Laid-Open Application DOS No. 2,118,283) is used, the stated by-products are obtained in substantially larger amount (cf. Examples 13 and 18).

Using the process according to the invention has the further advantage that single stereoisomers are obtained if single stereoisomers are used as starting materials. The isomerizations which frequently occur over hydrogenation catalysts (Houben-Weyl, "Methoden der Organischen Chemie", 4/2, pages 276–283) are not observed in the present instance.

Using the process according to the invention, the amine component can be employed in stoichiometric amount, based on the carbonyl compound, or in up to 10-fold molar excess.

Examples of suitable starting materials of the formula III are the following carbonyl compounds: 3-phenyl-2-methyl-prop-2-enal, 3-phenyl-2-methyl-propanal, 3-phenyl-3-methyl-prop-2-enal, 3-phenyl-3-methyl-propanal, 4-phenyl-but-3-en-2-one, 4-phenyl-butan-2-one, 3-(4'-methylphenyl)-2-methyl-prop-2-enal, 3-(4'-methylphenyl)-2-methylpropanal, 3-(4'-isopropylphenyl)-2-methyl-prop-2-enal, 3-(4'-isopropylphenyl)-2-methyl-propanal, 3-(4'-tertiary butylphenyl)-2-methyl-prop-2-enal, 3-(4'-tertiary butylphenyl)-2-methyl-propanal, 3-phenyl-2-ethyl-prop-2-enal, 3-phenyl-2-ethylpropanal, 3-phenyl-2-isopropyl-prop-2-enal, 3-phenyl-2-isopropyl-propanal, 3-(4'-isopropylphenyl)-3-methyl-prop-2-enal, 3-(4'-isopropylphenyl)-3-methylpropanal, 3-(4'-tertiary butylphenyl)-3-methyl-prop-2-enal, 3-(4'-tertiary butylphenyl)-3-methyl-propanal, 4-(4'-tertiary butylphenyl)-but-3-en-2-one, 4-(4'-tertiary butylphenyl)-butan-2-one, 3-(4'-methoxyphenyl)-2-methyl-prop-2-enal, 3-(4'-methoxyphenyl)-2-methyl-propanal, 3-(4'-isopropoxyphenyl)-2-methyl-prop-2-enal, 3-(4'-isopropoxyphenyl)-2-methyl-prop-2-enal, 3-(4'-cyclohexylphenyl)-2-methyl-prop-2-enal, 3-(4'-cyclohexylphenyl)-2-methylpropanal, 3-(4'-cyclopentylphenyl)-2-methyl-prop-2-enal and 3-(4'-cyclopentylphenyl)-2-methyl-propanal.

The known starting materials III can be prepared by an aldol condensation of appropriately substituted benzaldehydes with aliphatic aldehydes or ketones. The hydrogenated compounds are obtained from the unsaturated products by partial hydrogenation of the carbon-carbon double bond (cf. U.S. Pat. No. 2,976,321).

Examples of tertiary amines of the formula II which may be reacted by the process according to the invention are the following: pyrrolidine, piperidine, 2-methylpiperidine, 3-methylpiperidine, 4-methylpiperidine, 2,6-dimethylpiperidine, 3,5-dimethylpiperidine, 4-ethylpiperidine, morpholine, 2-methylmorpholine, 2-ethylmorpholine, 3-methylmorpholine, 2,6-dimethylmorpholine, 3,5-dimethylmorpholine, 2,5-dimethylmorpholine, 2,6-diethylmorpholine, piperazine, 1-methylpiperazine, hexamethyleneimine, 2,3-dimethylhexamethyleneimine, 3,5,5-trimethylhexamethyleneimine and 3,3,5-trimethylhexamethyleneimine.

The reaction can be carried out in the absence of solvents, or in the presence of solvents which are inert under the reaction conditions. Examples of suitable solvents are: methanol, ethanol, propanol, tetrahydrofuran, dioxane, anisole, ethylene glycol monomethyl ether, 1,2-dimethoxyethane, methyl tert.-butyl ether, cyclohexyl methyl ether, di-n-butyl ether, toluene and cyclohexane.

The reaction may be carried out either continuously or batchwise, and is preferably carried out in the liquid phase.

The catalyst system used in the process according to the invention contains palladium as the hydrogenating metal, and, as an added component, zinc, cadmium, manganese or a rare earth metal oxide, or a mixture of such oxides, one or more of the said additional components being present in addition to the palladium. The additives increase the selectivity of the hydrogenating catalyst.

For the purposes of the invention, rare earth metal oxides are the oxides of lanthanum (La), cerium (Ce), praseodymium (Pr), neodymium (Nd), samarium (Sm), europium (Eu), thulium (Tm), ytterbium (Yb) and lutetium (Lu). Amongst these, preferred rare earth metal oxides are $La_2O_3$, $Pr_2O_3$ and $Nd_2O_3$.

The catalyst system used according to the invention may contain the rare earth metal oxides in a pure form or in the form obtained industrially, i.e. as a mixture of the oxides of several rare earth metals.

Examples of suitable inert carriers, in addition to $Al_2O_3$, $SiO_2$ and active charcoal already mentioned, are aluminum silicates and magnesium silicates.

The palladium content of the catalyst, based on amount of carrier, is not critical and can vary within wide limits, but is advantageously from 0.05 to 15% by weight. An advantageous content of the additional component of the catalyst (zinc, cadmium, manganese or rare earth metal oxides) is from 0.01 to 10% by weight, based on carrier. The weight ratio of the additional catalyst components to the palladium metal may be, for example, from 400:1 to 1:150, preferably from 50:1 to 1:10. The catalyst is used, for example, as extrudates of 5 mm diameter and 10 mm length, or as a powder.

The catalyst may be prepared, for example, by impregnating the palladium-containing carrier with a solution of the rare earth metal carbonates and then heating the impregnated material.

The compounds prepared by the process according to the invention are known and may be used as intermediates for crop protection agents or as active ingredients in conventional crop protection agents (cf. German Laid-Open Applications DOS Nos. 2,752,096, DOS 2,752,135 and DOS 2,656,747).

In the Examples which follow, parts are by weight and bear the same relation to parts by volume as that of the kilogram to the liter.

EXAMPLE 1

A catalyst comprising 0.5% by weight of Pd and 5% by weight of $Pr_2O_3$ (95% pure $Pr_2O_3$, the remainder consisting of oxides of other rare earth metals) on $Al_2O_3$ as the carrier is introduced into a cylindrical reaction tube of capacity 500 parts by volume, and is heated at 130° C. Per hour, 60 parts of a mixture comprising 146 parts of 3-phenyl-2-methyl-prop-2-enal (α-methylcinnamaldehyde) and 115 parts of cis-2,6-dimethylmorpholline are passed over this catalyst bed. At the same time, 100,000 parts by volume of hydrogen under a pressure of 50 bar are passed, in the same direction, through the reaction tube. The reaction product issuing from the tube is cooled under pressure and is then let down. This gives 60 parts per hour of a crude product, which is purified by distillation. The distillation of 100 parts of crude product gives 77.5 parts of N-(3'-phenyl-2'-methylpropyl)-cis-2,6-dimethylmorpholine, boiling point 95° C./0.01 mm Hg, corresponding to a yield of 83% of theory.

EXAMPLE 2

A catalyst comprising 0.50% by weight of Pd, 0.11% by weight of Zn and 0.10% by weight of Cd on Al$_2$O$_3$ as the carrier is introduced into the same apparatus as described in Example 1, and is heated at 100° C. Per hour, 60 parts of a mixture comprising 146 parts of 3-phenyl-2-methylprop-2-enal (α-methylcinnamaldehyde) and 115 parts of cis-2,6-dimethylmorpholine are passed over this catalyst bed. Over the same period 100,000 parts by volume of hydrogen under a pressure of 50 bar are passed, in the same direction, through the reaction tube. The reaction product issuing from the tube is cooled under pressure and is then let down. This gives 60 parts per hour of a crude product, which is purified by distillation. The distillation of 100 parts of crude product gives 75.5 parts of N-(3'-phenyl-2'-methylpropyl)-cis-2,6-dimethylmorpholine, corresponding to 81% of theory.

EXAMPLE 3

Using the same apparatus and the same catalyst as in Example 1, a reaction is carried out at 120° C. with an hourly feed of 120 parts of a mixture which comprises 261 parts of methanol, 146 parts of 3-phenyl-2-methylprop-2-enal (α-methylcinnamaldehyde) and 115 parts of 2,6-dimethylmorpholine, containing 75% by weight of the cis-compound and 25% by weight of the trans-compound. Simultaneously with the above mixture, 100,000 parts by volume of hydrogen under a pressure of 50 bar are passed, in the same direction, through the reaction tube. The reaction product issuing from the tube is cooled under pressure and then let down. This gives 120 parts per hour of crude product, which is purified by distillation. The distillation of 200 parts of crude product gives 80.5 parts of N-(3'-phenyl-2'-methyl-propyl)-2,6-dimethylmorpholine, containing 75% by weight of cis-compound and 25% by weight of trans-compound, boiling point 155°–157° C./12 mm Hg. This corresponds to a yield of 86% of theory.

EXAMPLE 4

Using the same apparatus and the same catalyst as described in Example 1, a reaction is carried out at 130° C. with an hourly feed of 120 parts of a mixture which comprises 317 parts of methanol, 202 parts of 3-p-tertiary butylphenyl-2-methyl-prop-2-enal and 115 parts of cis-2,6-dimethylmorpholine. Simultaneously with the above mixture, 100,000 parts by volume of hydrogen under a pressure of 50 bar are passed, in the same direction, through the reaction tube. The reaction product issuing from the tube is cooled under pressure and then let down. This gives 120 parts per hour of crude product, which is purified by distillation. The distillation of 200 parts of crude product gives 88.5 parts of N-(3'-(p-tertiary butylphenyl)-2'-methyl-propyl)-cis-2,6-dimethylmorpholine, boiling point 206° C./18 mm Hg. This corresponds to a yield of 92.5% of theory.

EXAMPLE 5

A mixture of 153 parts of 3-p-tertiary butylphenyl-2-methyl-propanol, 70 parts of piperidine, 230 parts of methanol and 20 parts of catalyst, comprising 0.5% by weight of Pd and 5% by weight of Nd$_2$O$_3$ on Al$_2$O$_3$, is hydrogenated in a stirred autoclave of 1,000 parts by volume capacity, at 70° C. under a hydrogen pressure of 50 bar, until the pressure remains constant. The autoclave is then allowed to cool, the catalyst is filtered off and the filtrate is purified by distillation. 195 parts of N-(3'-(p-tertiary butylphenyl)-2'-methylpropyl)-piperidine, boiling point 117° C./0.2 mm Hg, are obtained. The yield is 94% of theory.

EXAMPLE 6

A mixture of 153 parts of 4-(p-tertiary butylphenyl)-butan-2-one, 115 parts of 2,6-dimethylmorpholine (75% cis-compound and 25% trans-compound), 270 parts of methanol and 20 parts of the catalyst described in more detail in Example 5 is hydrogenated, in the apparatus described in Example 5, at 140° C. and 50 bar hydrogen pressure, until the pressure remains constant. The autoclave is then allowed to cool, the catalyst is filtered off and the filtrate is purified by distillation. 195.5 parts of N-(4'-(p-tertiary butylphenyl)-but-2'-yl)-2,6-dimethylmorpholine (75% cis-compound and 25% trans-compound), boiling point 143° C./0.01 mm Hg, are obtained. The yield is 86% of theory.

EXAMPLE 7

The procedure followed is as described in Example 5, except that 2,2,4-trimethylazetidine is used as the amine component. The end product obtained is N-(3'-(p-tertiary butylphenyl)-2'-methyl-propyl)-2,2,4-trimethylazetidine, boiling point 134° C./0.3 mm Hg. The yield is 93% of theory.

EXAMPLE 8

The procedure followed is as described in Example 5, except that the starting materials are 3-p-tertiary butylphenyl-2-methyl-prop-2-enal as the carbonyl component and 2,3-dimethylhexamethyleneimine as the amine component. The end product obtained is N-(3'-(p-tertiary butylphenyl)-2'-methyl-propyl)-2,3-dimethylhexamethyleneimine, boiling point 144° C./0.01 mm Hg. The yield is 95% of theory.

EXAMPLE 9

The procedure followed is as described in Example 5, except that pyrrolidine is used as the amine component. The end product obtained is N-(3'-(p-tertiary butylphenyl)-2'-methyl-propyl)-pyrrolidine, boiling point 115° C./0.3 mm Hg. The yield is 96% of theory.

EXAMPLE 10

A mixture of 190 parts of 3-p-isopropylphenyl-3-methylpropanal, 111 parts of 2-methylmorpholine, 300 parts of methanol and 20 parts of catalyst, comprising 0.5% by weight of Pd, 0.11% by weight of Zn and 0.1% by weight of Cd on Al$_2$O$_3$, is hydrogenated in a stirred autoclave of 1,000 parts by volume capacity, at 120° C. under a hydrogen pressure of 50 bar, until the pressure remains constant. The autoclave is then allowed to cool, the catalyst is filtered off and the filtrate is purified by distillation. 266 parts of N-(3'-(p-isopropylphenyl)-3'-methylpropyl)-2-methylmorpholine, boiling point 122° C./0.05 mm Hg are obtained. The yield is 82% of theory.

EXAMPLE 11

The procedure followed is as described in Example 10, except that the starting materials used are 3-p-methoxyphenyl-2-methyl-propanal as the carbonyl component and cis-2,6-dimethylmorpholine as the amine component. This gives N-(3'-p-methoxyphenyl)-2'-methylpropyl)-cis-2,6-dimethylmorpholine, boiling point 129° C./0.1 mm Hg, as the end product. The yield is 82% of theory.

EXAMPLE 12

A mixture of 101 parts of 3-p-tertiary butylphenyl-2-methyl-prop-2-enal and 61 parts of cis-2,6-dimethylmorpholine, dissolved in 900 parts of methanol, is hydrogenated, in a stirred apparatus of capacity 2,000 parts by volume, in the presence of 5 parts of a hydrogenation catalyst comprising 10% by weight of Pd, 0.11% by weight of Zn and 0.1% by weight of Cd on $Al_2O_3$, at 30° C. under atmospheric pressure, until the absorption of hydrogen has ceased. The catalyst is filtered off and the filtrate is worked up by distillation. This gives 141 parts of N-(3'-(p-tertiary butylphenyl)-2'-methylpropyl)-cis-1,6-dimethylmorpholine, boiling point 206° C./18 mm Hg, corresponding to a yield of 93%.

EXAMPLE 13—COMPARATIVE EXAMPLE

Except for the use of a catalyst comprising 0.36% by weight of Pd, 4.8% by weight of Ag and 1.05% by weight of Mn on $SiO_2$, the procedure followed is entirely as described in Example 1, using the same starting materials and under the same reaction conditions. The reaction product obtained has the following composition, according to analysis by gas chromatography: 22% by weight of N-(3'-phenyl-2'-methyl-propyl)-cis-2,6-dimethylmorpholine, 14% by weight of N-(3'-phenyl-2'-methyl-prop-2'-enyl)-cis-2,6-dimethylmorpholine, 36.2% by weight of 3-phenyl-2-methylpropanol and 27.8% by weight of cis-2,6-dimethylmorpholine.

EXAMPLE 14

A mixture of 2,500 parts by volume of methanol, 366 parts of cis-2,6-dimethylmorpholine, 606 parts of 3-p-tertiary butylphenyl-2-methyl-prop-2-enal and 35 parts of catalyst, comprising 0.5% by weight of Pd, 5% by weight of $Pr_2O_3$, 1% by weight of Mn, remainder $Al_2O_3$, is hydrogenated stepwise, in a stirred autoclave of 5,000 parts by volume capacity, first at 50° C. under 50 bar hydrogen pressure, then at 90° C. under the same pressure and finally at 120° C. under the same pressure, until no further hydrogen is absorbed. The autoclave is then allowed to cool, the catalyst is filtered off and the filtrate is purified by distillation. 856 parts of N-(3'-p-tertiary butylphenyl-2'-methyl-propyl)-cis-2,6-dimethylmorpholine, boiling point 206° C./24 mbar, are obtained. This corresponds to a yield of 94% of theory (based on 3-p-tertiary butylphenyl-2-methyl-prop-2-enal).

EXAMPLE 15

A stirred autoclave of 1,000 parts by volume capacity is charged with a mixture of 153 parts of 3-p-tertiary butylphenyl-2-methyl-propanal, 75 parts of hexamethyleneimine, 230 parts of methanol and 20 parts of a catalyst which comprises 0.5% of Pd, 5% of $Pr_2O_3$ and 1% of Mn on $Al_2O_3$. The mixture is then hydrogenated at 90° C. and 50 bar hydrogen pressure until the pressure remains constant. The autoclave is then allowed to cool, the catalyst is filtered off and the filtrate is purified by distillation. This gives 207 parts of N-[3-(p-tertiary butylphenyl)-2'-methyl-propyl]-hexamethyleneimine, boiling point 130° C./0.26 mbar.

The yield is 96% of theory (based on 3-p-tertiary butylphenyl-2-methyl-propanal).

EXAMPLE 16

The procedure followed is as described in Example 14, except that 3-phenyl-2-methyl-prop-2-enal is used as the carbonyl component. The end product obtained is N-(3'-phenyl-2'-methylpropyl)-cis-2,6-dimethylmorpholine, boiling point 95° C./0.05 mbar. The yield is 93% of theory.

EXAMPLE 17

The procedure followed is as described in Example 15, except that 3,5-dimethylpiperidine is used as the amine component. The end product obtained is N-[3'-(p-tertiary butylphenyl)-2'-methylpropyl]-3,5-dimethylpiperidine, boiling point 135° C./0.4 mbar.

EXAMPLE 18—COMPARATIVE EXAMPLE

Except for the use of a catalyst comprising 0.36% by weight of Pd, 4.8% by weight of Ag and 1.05% by weight of Mn on $SiO_2$, the procedure followed is entirely as described in Example 14, using the same starting materials and the same reaction conditions. The reaction product obtained has the following composition, according to analysis by gas chromatography: 46% by weight of N-(3'-p-tertiary butylphenyl-2'-methyl-propyl)-cis-2,6-dimethylmorpholine, 25% by weight of N-(3'-p-tertiary butylphenyl-2'-methyl-prop-2'-enyl)-cis-2,6-dimethylmorpholine, 18% by weight of 3-p-tertiary butylphenyl-2-methyl-propanol and 11% by weight of cis-2,6-dimethylmorpholine.

We claim:

1. A process for the preparation of an aralkylamine of the formula I

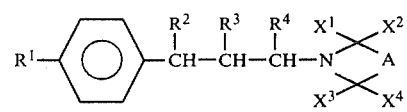

where

R[1] is hydrogen, an aliphatic hydrocarbon radical of 1 to 10 carbon atoms, a cycloaliphatic radical of 5 to 7 carbon atoms or alkoxy of 1 to 6 carbon atoms, R[2], R[3] and R[4] are hydrogen or alkyl of 1 to 4 carbon atoms, X[1], X[2], X[3] and X[4] are hydrogen or alkyl of 1 to 4 carbon atoms, A is

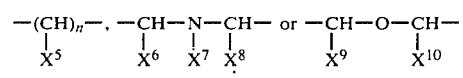

X[5], X[6], X[7], X[8], X[9] and X[10] are hydrogen or alkyl of 1 to 4 carbon atoms and n is 2, 3 or 4, by reacting a secondary amine of the formula II

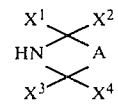

where

X[1], X[2], X[3], X[4] and A have the above meanings with a carbonyl compound of the formula III

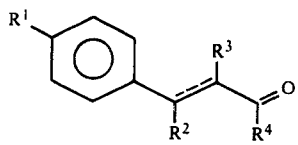
where
$R^1$, $R^2$, $R^3$ and $R^4$ have the above meanings and the bond shown in broken lines is a double bond or a single bond,
wherein the reaction is carried out in the presence of hydrogen and of a hydrogenation catalyst which consists essentially of palladium, mixed with zinc, cadmium, manganese and/or a rare earth metal oxide, on an inert carrier.
* * * * *